(12) United States Patent
Arimoto et al.

(10) Patent No.: US 9,897,485 B2
(45) Date of Patent: Feb. 20, 2018

(54) ABSORPTION SPECTROMETER

(71) Applicant: HORIBA, Ltd., Kyoto-shi, Kyoto (JP)

(72) Inventors: Kimihiko Arimoto, Kyoto (JP); Takuya Onoda, Kyoto (JP); Tatsuya Nakahara, Kyoto (JP)

(73) Assignee: HORIBA, Ltd., Kyoto-shi, Kyoto (JP)

( * ) Notice: Subject to any disclaimer, the term of this patent is extended or adjusted under 35 U.S.C. 154(b) by 0 days.

(21) Appl. No.: 15/355,399

(22) Filed: Nov. 18, 2016

(65) Prior Publication Data
US 2017/0167918 A1   Jun. 15, 2017

(30) Foreign Application Priority Data
Dec. 14, 2015 (JP) .................................. 2015-243568

(51) Int. Cl.
| | | |
|---|---|---|
| G01J 3/00 | (2006.01) |
| G01J 3/02 | (2006.01) |
| G01J 3/18 | (2006.01) |
| G01J 3/42 | (2006.01) |
| G01J 3/28 | (2006.01) |
| G01N 21/27 | (2006.01) |

(52) U.S. Cl.
CPC ............... *G01J 3/0297* (2013.01); *G01J 3/18* (2013.01); *G01J 3/28* (2013.01); *G01J 3/42* (2013.01); *G01N 21/27* (2013.01); *G01J 3/0208* (2013.01)

(58) Field of Classification Search
CPC .... G01J 1/58; G01J 3/0297; G01J 3/18; G01J 3/28; G01J 3/42; G01J 3/0208; G01N 1/00; G01N 21/03; G01N 21/27
See application file for complete search history.

(56) References Cited

U.S. PATENT DOCUMENTS

2014/0185049 A1* 7/2014 Yada .................... G01N 21/274
                                                         356/408

FOREIGN PATENT DOCUMENTS

JP        2014126529 A      7/2014

* cited by examiner

*Primary Examiner* — Jamil Ahmed
(74) *Attorney, Agent, or Firm* — Alleman Hall Creasman & Tuttle LLP

(57) ABSTRACT

In order to reduce a variation in the light amount of light detected in every reference measurement cycle in an absorption spectrometer 1, it is adapted to tilt at least one surface selected from among incident surfaces and emitting surfaces of all translucent members constituting a reference cell with respect to the light axis of light traveling along a light path.

6 Claims, 5 Drawing Sheets

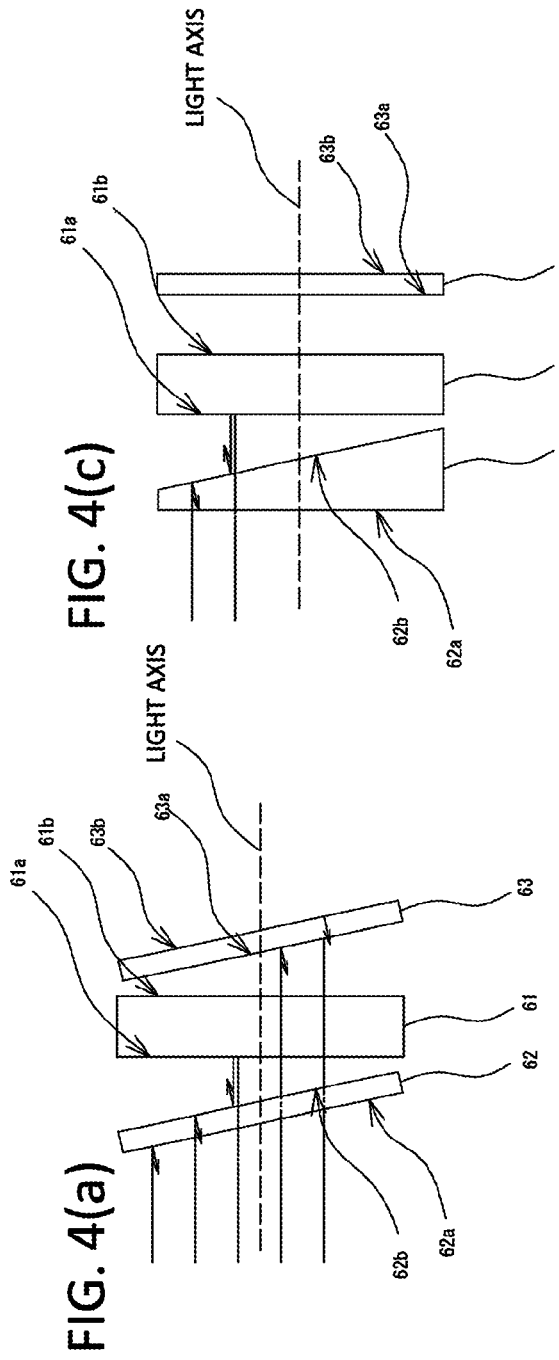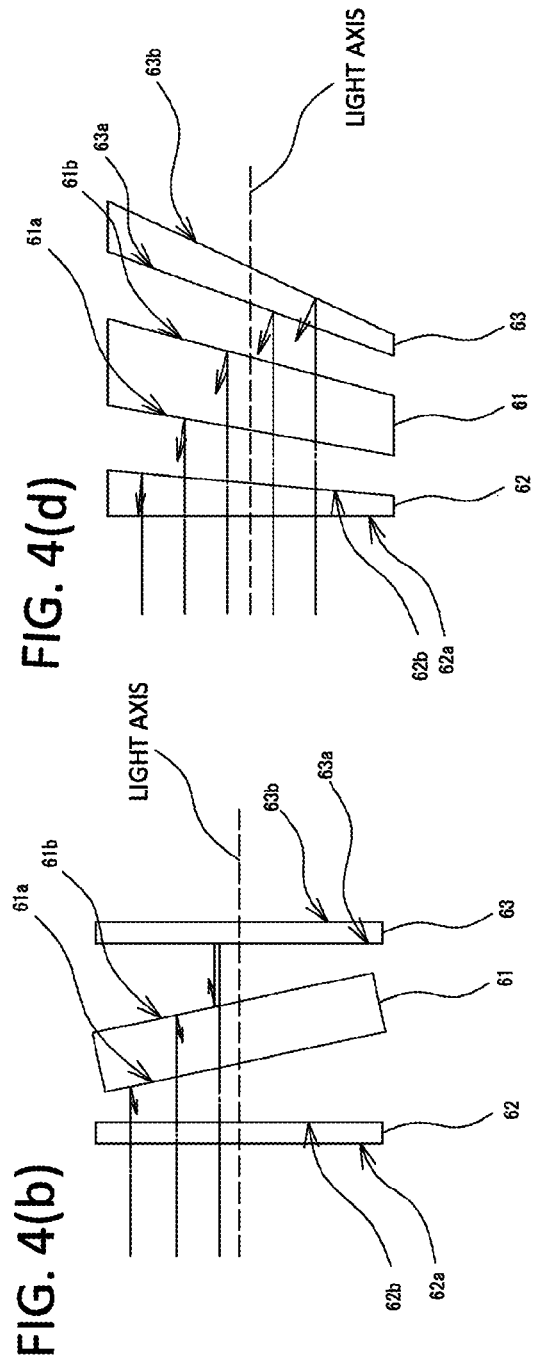

ABSORPTION SPECTROMETER

TECHNICAL FIELD

The present invention relates to an absorption spectrometer.

BACKGROUND ART

As well known, in a semiconductor manufacturing process, the concentration of a chemical used in each processing step affects the quality of semiconductor devices, and therefore the state of a change in the concentration is constantly monitored using an absorption spectrometer to manage so as to keep the concentration of the chemical constant.

Meanwhile, as a conventional absorption spectrometer, for example, as an absorption spectrometer disclosed in Patent Literature 1, there is one including: a light source; a light detector adapted to detect light emitted from the light source; and a sample cell and reference cell that can be switched to each other and alternately arranged either a measurement position positioned in a light path of the light passing between the light source and the light detector or a retracted position retracted from the measurement position. In addition, the absorption spectrometer is adapted to detect, by the light detector, light passing through a dimming element contained in the reference cell in a state of arranging the reference cell in the measurement position (reference measurement), also detect, by the light detector, light passing through a sample (a chemical) contained in the sample cell in a state of arranging the sample cell in the measurement position (sample measurement), and on the basis of pieces of light amount data on the lights detected in the both types of measurement, measure the concentration of each component contained in the sample.

On the other hand, improvement in the performance of semiconductor devices is directly linked with miniaturization. For this reason, in recent years, in order to achieve further miniaturization, various types of chemicals used in a semiconductor manufacturing process have tended to be diluted. However, as the concentration of a chemical is decreased, a variation of the concentration more significantly affects the quality of semiconductor devices as compared with the case where the chemical concentration is high. Accordingly, in order to make it possible to accurately measure even the concentration of a diluted chemical, further improvement in the accuracy of an absorption spectrometer has been demanded.

Therefore, the present inventor has examined a conventional absorption spectrometer in detail in order to respond to the demand. As a result, the present inventor has found the possibility that a variation in reference light amount, which has been thought to be caused by a variation in the light amount of light emitted from a light source, is significantly contributed to by another cause.

A description will be given in detail.

The conventional absorption spectrometer employs a moving mechanism adapted to, when moving a reference cell between a measurement position and a retracted position, slide the reference cell along a guide bridging between the both positions.

Using the conventional absorption spectrometer, an experiment that every 10 minutes, reciprocated the reference cell between the measurement position and the retracted position, and rearranged the reference cell in the measurement position to measure the absorbance of the reference cell was performed. As a result, as illustrated in an experimental result in FIG. 3, it was confirmed that in every reference measurement cycle, the absorbance largely varied. The present inventor has first known that the variation is mainly caused by a large variation in the measurement intensity of reference light. Note that in this experiment, light emitted from a light source was converted into parallel light through a collimator optical system and then passed through the reference cell. Also, the normalized absorbance in FIG. 3 was obtained by performing normalization, i.e., making the maximum deviation from the average value of absorbances in the conventional absorption spectrometer equal to 1. Further, the absorbance in the present embodiment was obtained by after the same normalization as above, adding 2 for ease of viewing a graph.

For now, the specific mechanism why the measurement intensity of the reference light fluctuates every time the reference cell is moved is not clarified.

However, the present inventor is considering that when a reflection type dimming element having a small time-dependent change was used in place of an absorption type dimming element conventionally used in a reference cell, a variation in the light amount of light detected in every reference measurement cycle more remarkably appeared, and therefore every time the reference cell is moved and rearranged, the attitude of the dimming element may slightly shift to cause the light amount variation of the reference light. Specifically, the present inventor is considering that part of the cause for the light amount variation is that the effect of multireflection caused by reflection lights generated at the incident and emitting surfaces of the dimming element may change, and as a result, the light amount of light detected in every reference measurement cycle, which is supposed to be constant, may vary every time the reference cell is positioned in the measurement position.

CITATION LIST

Patent Literature

Patent Literature 1: Japanese Unexamined Patent Publication JP-A 2014-126529

SUMMARY OF INVENTION

Technical Problem

Therefore, the main object of the present invention is to reduce a variation in the light amount of light detected in every reference measurement cycle in an absorption spectrometer.

Solution to Problem

That is, an absorption spectrometer according to the present invention includes: a light source; a light detector adapted to detect light emitted from the light source; a sample cell adapted to move between a sample measurement position positioned in a light path of the light passing between the light source and the light detector or a sample retracted position retracted from the sample measurement position and be selectively arranged either the sample measurement position and the sample retracted position; and a reference cell adapted to move between a reference measurement position positioned in the light path of the light passing between the light source and the light detector or a reference retracted position retracted from the reference measurement position and be selectively arranged either the reference measurement position and the reference retracted position, and contain at least one translucent member that transmits the light traveling along the light path from an incident surface to an emitting surface in a state of being arranged in the reference measurement position. In addition, at least one surface selected from among incident surfaces and emitting surfaces of all translucent members constituting the reference cell is tilted with respect to the light axis of the light traveling along the light path. Also, the reference cell is adapted to be slidable along a guide bridging between the reference measurement position and the reference retracted position.

As the translucent member to be contained in the reference cell, a member such as a dimming member that reduces the light amount of the light passing between the light source and the light detector depending on the light amount of light detected in sample measurement, or an anticorrosion member for protecting the dimming member from a chemical atmosphere is conceivable. Also, as a configuration adapted to contain a dimming member and/or an anticorrosion member in the reference cell, a configuration adapted to contain a single dimming member in the reference cell, or a configuration adapted to contain a dimming member and a pair of anticorrosion members in the reference cell, and arrange one of the anticorrosion members on an incident surface side of the dimming member as well as arranging the other anticorrosion member on an emitting surface side of the dimming member is conceivable. Note that diming members include an absorption type one and a reflection type one, and any of them is possible. Further, specific examples of the dimming member include, but without limitation to, optical glass (reflection type), and specific examples of the anticorrosion member include, but without limitation to, sapphire.

Also, it is conceivable to pass the light emitted from the light source through a collimator optical system to convert to parallel light, and then pass the parallel light through the reference cell. Alternatively, it is also conceivable to convert the light emitted from the light source to nonparallel converging light through a condensing optical system, and then pass the converging light through the reference cell.

Further, the reference cell may be one integrated with or separated from the sample cell. In the case where the reference cell and the sample cell are integrated with each other, it is necessary to provide only one moving mechanism, and therefore the number of parts can be reduced to reduce cost.

Note that "at least one surface selected from among incident surfaces and emitting surfaces of all translucent members constituting the reference cell is tilted with respect to the light axis of the light traveling along the light path" means, in other words, that at least one surface selected from among the incident surfaces and emitting surfaces of all the translucent members constituting the reference cell is rotated from a state of being positioned vertically to the light axis of the light traveling along the light path in any one of a clockwise direction and an anticlockwise direction and consequently tilted, and at the time of reference measurement, the surface is constantly kept in a state of being rotated in the one direction and tilted with respect to the light axis.

In such a configuration, even when the attitude of any translucent member contained in the reference cell is shifted every time the reference cell is arranged in the reference measurement position, reflection light generated at the surface tilted with respect to the light axis of the light traveling along the light path among the incident surfaces and emitting surfaces of all the translucent members constituting the reference cell travels in a direction crossing the light axis, and therefore the effect of multireflection caused by the reflection light can be reduced. As a result, a variation in the light amount of light detected in every reference measurement cycle can be suppressed, and therefore even in the case of a diluted chemical, the concentration of each component contained in the chemical can be accurately measured.

Also, it is desirable that at least one pair of surfaces selected from among the incident surfaces and emitting surfaces of all the translucent members constituting the reference cell is parallel, and the paired surfaces are both tilted with respect to the light axis of the light traveling along the light path. Further, it is desirable that the incident surfaces and emitting surfaces of all the translucent members constituting the reference cell are parallel.

Still further, it is desirable that at least one pair of surfaces selected from among the incident surfaces and emitting surfaces of all the translucent members constituting the reference cell is nonparallel, and any one or both of the paired surfaces are tilted with respect to the light axis of the light traveling along the light path. Yet further, it is desirable that the incident surfaces and emitting surfaces of all the translucent members constituting the reference cell are nonparallel.

In such a configuration, even when the attitude of any translucent member contained in the reference cell is shifted every time the reference cell is arranged in the reference measurement position, the number of surfaces tilted with respect to the light axis of the light traveling along the light path among the incident surfaces and emitting surfaces of all the translucent members constituting the reference cell is increased, and therefore the effect of multireflection caused by reflection lights generated at the respective surfaces can be reduced correspondingly. As a result, the variation in the light amount of light detected in every reference measurement cycle can be more largely suppressed. Note that the term "nonparallel" also includes nonparallelism that for example, when placing an anticorrosion member so as to face to an incident surface or emitting surface of a dimming member through a packing, accidentally occurs due to design accuracy preventing the uniformity of force pressing the anticorrosion member against the dimming member side.

Advantageous Effects of Invention

According to the present invention configured as described above, a variation in the light amount of light detected in every reference measurement cycle can be reduced.

BRIEF DESCRIPTION OF DRAWINGS

FIGS. 4(a) to 4(d) are schematic diagrams illustrating translucent members to be contained in a reference cell in each of other variations of the present invention.

DESCRIPTION OF EMBODIMENTS

In the following, the absorption spectrometer according to the present invention will be described with reference to the drawings.

An absorption spectrometer 100 of the present embodiment is one that is provided intervening in, for example, a chemical pipe for supplying a chemical such as hydrofluoric acid in a semiconductor manufacturing apparatus, and measures the concentration of the chemical (sample) such as hydrofluoric acid by a spectrometric method. In addition, the concentration of the chemical used in the semiconductor manufacturing apparatus is managed using the concentration measured by the absorption spectrometer.

Figure 1:
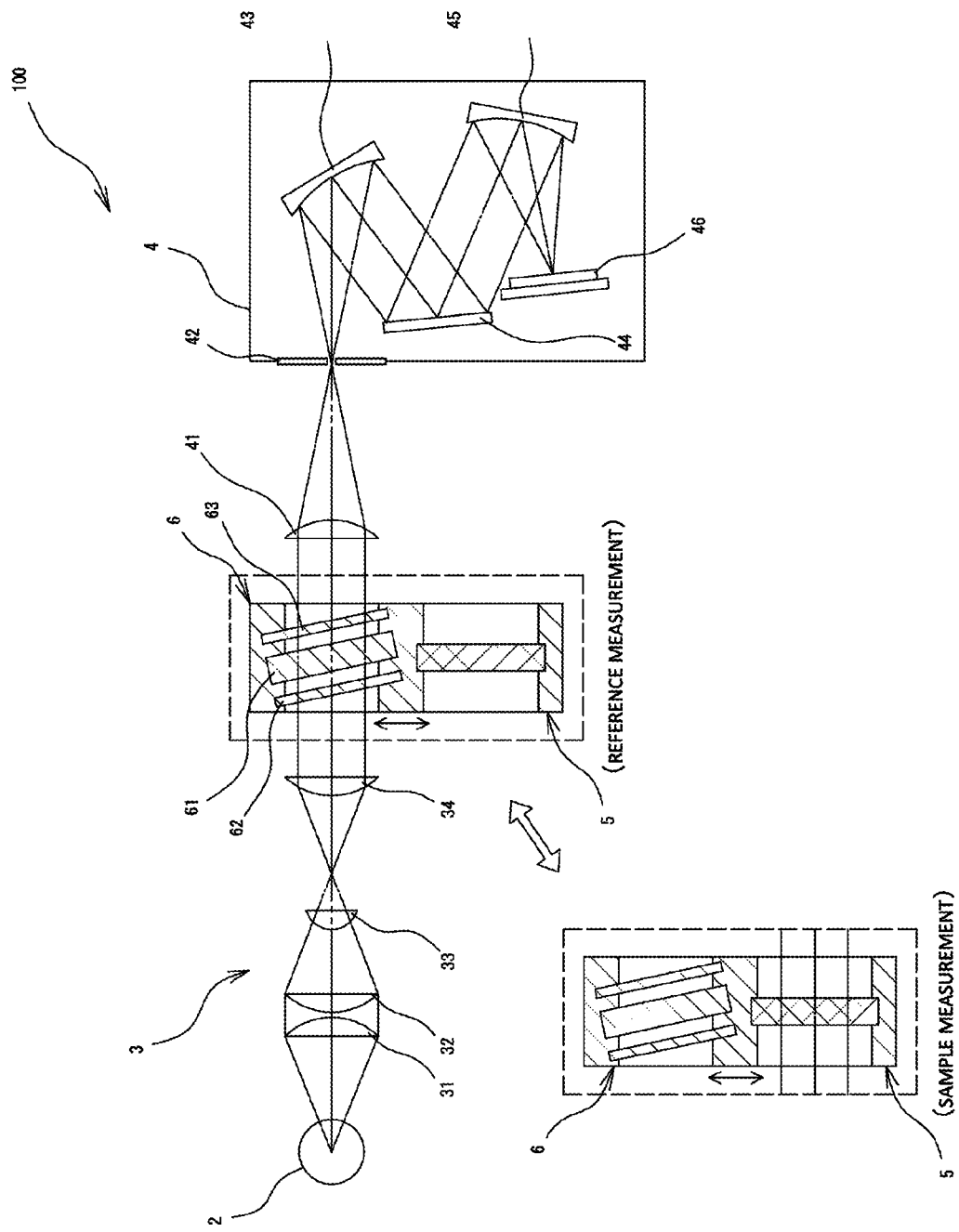
FIG. 1 is an overall conceptual diagram conceptually illustrating the configuration of an absorption spectrometer in one embodiment of the present invention.

As illustrated in FIG. 1, the absorption spectrometer 100 includes: a light source 2; a collimator optical system 3 adapted to convert light emitted from the light source 2 into parallel light; a light detector 4 adapted to detect light that is the parallel light produced by the collimator optical system 3; a sample cell 5 that can be selectively positioned either a sample measurement position positioned in a light path of the light passing between the light source 2 (collimator optical system 3) and the light detector 4 and a retracted position retracted from the sample measurement position; and a reference cell 6 that can be selectively positioned either a reference measurement position positioned in the light path of the light passing between the light source 2 and the light detector 4 and a retracted position retracted from the reference measurement position.

The light source 2 is a continuous spectrum light source including, for example, a halogen lamp and the like.

The collimator optical system 3 is one that converts the light emitted from the light source into the parallel light through at least one lens provided in an emission direction of the light source. The collimator optical system 3 in the present embodiment is configured by combining four plano-convex lenses 31, 32, 33, and 34.

The light detector 4 is one that disperses the light, which is the parallel light produced by the collimator optical system 3, into lights having respective wavelengths to detect the light on a wavelength component basis. Also, the light detector 4 includes: a condenser lens 41 that condenses light having transmitted through the sample cell 5 or the reference cell 6; an incident slit 42 that is provided near a focal point position of light resulting from the condensing by the condenser lens 41; a collimating mirror 43 that converts the light incident through the incident slit 42 into parallel light again; a diffraction grating 44 that disperses the parallel light received from the collimating mirror 43 on a wavelength basis; a camera mirror 45 that condenses lights having respective wavelengths resulting from the dispersing by the diffraction grating 44; and a multichannel detector 46 that detects the lights having the respective wavelengths condensed by the camera mirror 45. In addition, the concentration of each component contained in the chemical is calculated on the basis of a light intensity signal obtained by the multichannel detector 46. The multichannel detector 46 is one adapted to detect light in a near-infrared region. Alternatively, the multichannel detector 46 may be one adapted to detect light in a visible region or an ultraviolet region.

The sample cell 5 is a flow cell type one provided in a circulation path formed by the chemical pipe connected to a chemical tank of the semiconductor manufacturing apparatus. Also, the sample cell 5 is adapted to be selectively movable by the below-described moving mechanism to the sample measurement position positioned in the light path of the parallel light passing between the light source 2 and the light detector 4 or the sample retracted position retracted from the sample measurement position.

The reference cell 6 is one for decreasing a light intensity signal obtained by the light detector 4 at the time of reference cell measurement depending on a light intensity signal obtained by the light detector 4 at the time of sample cell measurement. Also, the reference cell 6 is adapted to be selectively movable by the below-described moving mechanism to the reference measurement position positioned in the light path of the parallel light passing between the light source 2 and the light detector 4 or the retracted position retracted from the reference measurement position.

Figure 2:
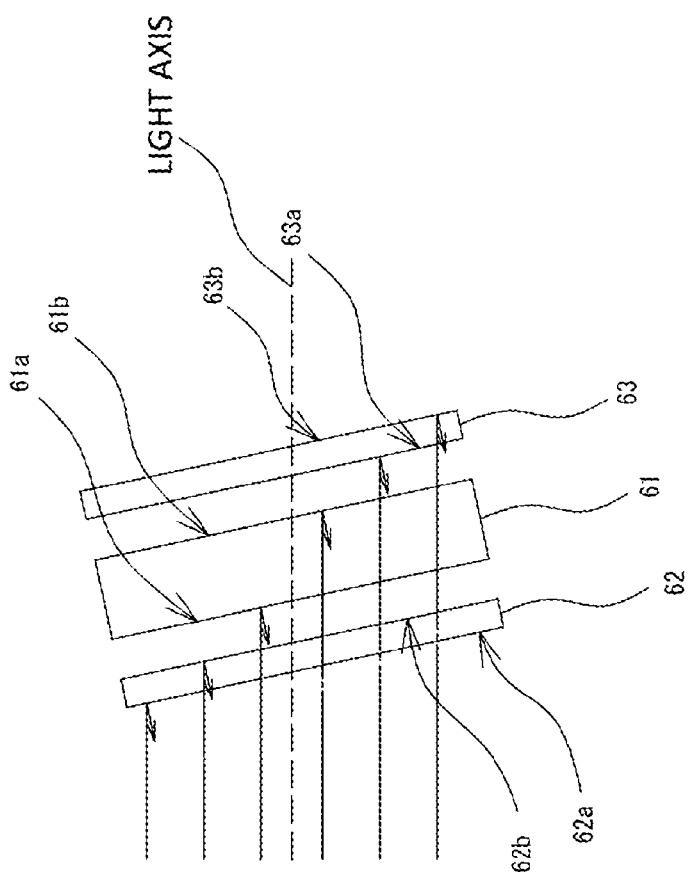
FIG. 2 is a schematic diagram illustrating translucent members to be contained in a reference cell in the same embodiment.

The reference cell 6 in the present embodiment contains three translucent members 61, 62, and 63. One of the three translucent members 61, 62, and 63 is a dimming member 61 that reduces the light amount of the light (the light transmitting through the reference cell 6) passing between the light source 2 and the light detector 4, and the other two are anticorrosion members 62 and 63 that protects the dimming member 61 from a chemical atmosphere. In addition, as illustrated in FIG. 2, the three translucent members 61, 62, and 63 have incident surfaces 61a, 62a, and 63a on which the light traveling from the light source 2 side toward the light detector 4 side is incident, and emitting surfaces 61b, 62b, and 63b from which the light emits, and are of plate shapes of which the incident surfaces 61a, 62a, and 63a and the emitting surfaces 61b, 62b, and 63b are parallel positioned, respectively. Further, the three translucent members 61, 62, and 63 are all contained in the reference cell 6 in a state of being tilted at the same angle with respect to the light axis of the light passing between the light source 2 and the light detector 4. In addition to this, the one anticorrosion member 62 is arranged on the incident surface 61a side of the dimming member 61 at an interval, and the other anticorrosion member 63 is arranged on the emitting surface 61b side of the dimming member 61 at an interval. In doing so, the incident surfaces 61a, 62a, and 63a and emitting surfaces 61b, 62b, and 63b of the three translucent members 61, 62, and 63 constituting the reference cell 6 are all in the state of being tilted at the same angle with respect to the light axis of the light passing between the light source 2 and the light detector 4.

The moving mechanism is one adapted to move any of the sample cell 5 and the reference cell 6 to selectively arrange it in the measurement position (the sample measurement position for the sample cell 5 or the reference measurement position for the reference cell 6) or the retracted position (the sample retracted position for the sample cell 5 or the reference retracted position for the reference cell 6). The sample cell 5 and the reference cell 6 in the present embodiment are integrated parallel to the light path of the light passing between the light source 2 and the light detector 4, and the moving mechanism is configured to integrally move the sample cell 5 and the reference cell 6 back and forth in a direction orthogonal to the light path. In doing so, when one of the cells is positioned in the measurement position, the other cell is in a state of being positioned in the retracted position. In addition, as the moving mechanism, although not illustrated, for example, a driving motor, a rack-and-pinion mechanism adapted to convert rotational motion obtained by the driving motor to linear motion, and a structure adapted to slide the sample cell 5 and the reference cell 6 along a guide through the linear motion obtained by the rack-and-pinion mechanism can be used.

In the present embodiment, since the incident surfaces 61a, 62a, and 63a and emitting surfaces 61b, 62b, and 63b of all the translucent members 61, 62, and 63 constituting the reference cell 6 are tilted at the same angle with respect to the light axis of the light passing between the light source 2 and the light detector 4, as illustrated in FIG. 2, when the light traveling from the light source 2 side toward the light detector 4 side at the time of reference measurement is incident on the incident surfaces 61a, 62a, and 63a and emitting surfaces 61b, 62b, and 63b of the respective translucent members 61, 62, and 63, reflection lights generated at the respective surfaces 61a, 62s, 63a, 61b, 62b, and 63b all travel in a direction crossing the light axis. This makes it possible to suppress the effect of multireflection caused by the reflection lights generated at the respective surfaces 61a, 62a, 63a, 61b, 62b, and 63b and therefore reduce a variation in the light amount of light detected in every reference measurement cycle.

Figure 3:
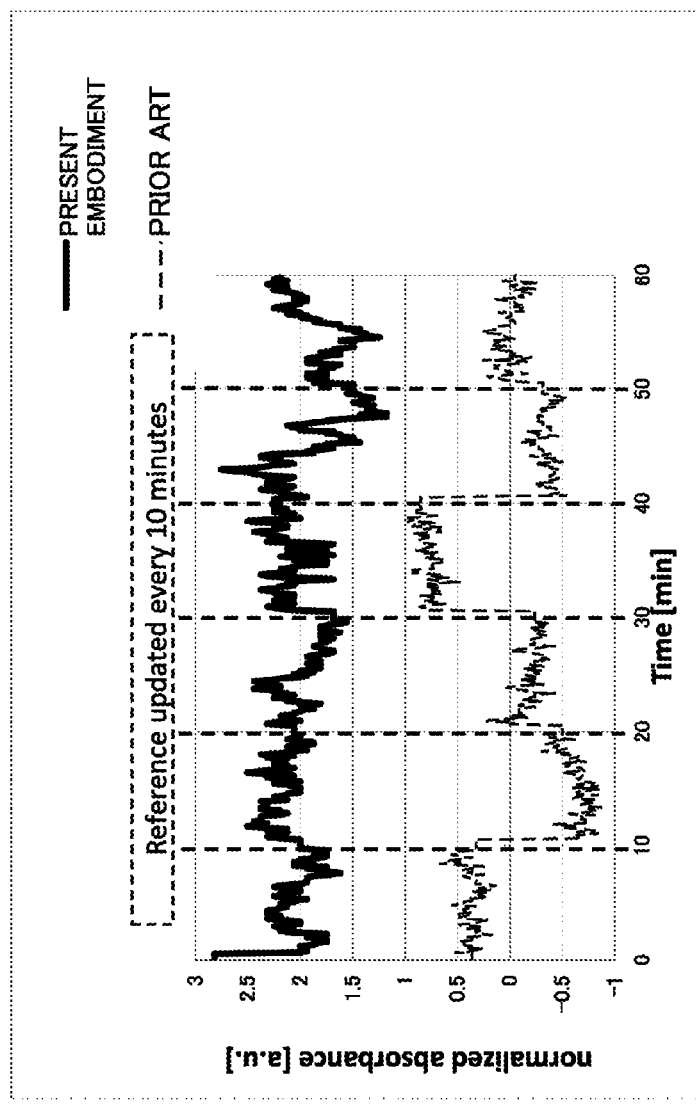
FIG. 3 is a graph illustrating the result of a comparative experiment between the configuration in the same embodiment and a conventional configuration.

FIG. 3 illustrates an experimental result. As described above, the experimental result shows a comparison of a variation in the measured light amount of reference light between the above-described conventional absorption spectrometer of which the reference cell is designed not to be tilted (in practice, there is a possibility that the reference cell is slightly tilted due to machining accuracy or the like; however, the term "tilt" here does not include such an unexpected tilt) and the absorption spectrometer 100 of the present embodiment. It can be seen from the experimental result that as compared with the conventional absorption spectrometer, the absorption spectrometer of the present embodiment clearly reduces the variation in the light amount of light detected in every reference measurement cycle.

<Other Variations>

Note that the present invention is not limited to the above-described embodiment.

For example, the translucent members contained in the reference cell 6 may be such that as illustrated in FIG. 4(a), among the three translucent members 61, 62, and 63 in the above-described embodiment, the dimming member 61 is contained in a state where the incident surface 61a and the emitting surface 61b are not tilted with respect to the light axis of the light passing through the reference cell 6, and the anticorrosion members 62 and 63 are contained in a state where the incident surfaces 62a and 63a and the emitting surfaces 62b and 63b are tilted at the same angle with respect to the light axis. In this case, reflection lights generated at the incident surfaces 62a and 63a and emitting surfaces 62b and 63b of the anticorrosion members 62 and 63 all travel in a direction crossing the light axis. Also, a reflection light generated at the incident surface 61a of the dimming member 61 is reflected at the emitting surface 62b of the anticorrosion member 62 facing to the incident surface 61a of the dimming member 61 side by side on the light source 2 side so as to travel in a direction crossing the light axis. As a result, the effect of multireflection can be suppressed to reduce the variation in the light amount of light detected in every reference measurement cycle.

Also, as illustrated in FIG. 4(b), it may be adapted to, among the three translucent members 61, 62, and 63 in the above-described embodiment, contain the dimming member 61 in a state where the incident surface 61a and the emitting surface 61b are tilted with respect to the light axis of the light passing through the reference cell 6, and contain the anticorrosion members 62 and 63 in a state where the incident surfaces 62a and 63a and the emitting surfaces 62b and 63b are not tilted with respect to the light axis. In this case, reflection lights generated at the incident surface 61a and emitting surface 61b of the dimming member 61 both travel in a direction crossing the light axis. Also, a reflection light generated at the incident surface 63a of the anticorrosion member 63 is reflected at the emitting surface 61b of the dimming member 61 facing to the incident surface 63a of the anticorrosion member 63 side by side on the light source 2 side so as to travel in a direction crossing the light axis. As a result, the effect of multireflection can be suppressed to reduce the variation in the light amount of light detected in every reference measurement cycle.

Further, as illustrated in FIG. 4(c), it may be adapted to, among the three translucent members 61, 62, and 63 in the above-described embodiment, change the anticorrosion member 62 to a plate-shaped one formed so as to make the incident surface 62a and the emitting surface 62b nonparallel, contain the anticorrosion member 62 in a state where the incident surface 62a is not tilted with respect to the light axis of the light passing through the reference cell 6 but the emitting surface 62b is tilted with respect to the light axis, and contain the dimming member 61 and the anticorrosion member 63 in a state where the incident surfaces 61a and 63a and the emitting surfaces 61b and 63b are not tilted with respect to the light axis. In this case, a reflection light generated at the emitting surface 62b of the anticorrosion member 62 travels in a direction crossing the light axis, and a reflection light generated at the incident surface 61a of the dimming member 61 is reflected at the emitting surface 62b of the anticorrosion member 62 facing to the incident surface 61a of the dimming member 61 side by side on the light source 2 side so as to travel in a direction crossing the light axis. As a result, the effect of multireflection can be suppressed to reduce the variation in the light amount of light detected in every reference measurement cycle.

Still further, as illustrated in FIG. 4(d), it may be adapted to change all the three translucent members 61, 62, and 63 in the above-described embodiment to plate-shaped ones formed so as to make the incident surfaces 61a, 62a, and 63a and the emitting surfaces 61b, 62b, and 63b positioned in a nonparallel manner, respectively, and contain the three translucent members 61, 62, and 63 in a state where only the incident surface 62a of the anticorrosion member 62 is not tilted with respect to the light axis of the light passing through the reference cell 6 and the surfaces 61a, 63a, 61b, 62b, and 63b except for the incident surface 62a of the anticorrosion member 62 are respectively tilted at difference angles with respect to the light axis. In doing so, all the surfaces 61a, 62a, 63a, 61b, 62b, and 63b come to states of crossing the light axis at different angles, respectively. In this case, reflection lights generated at the surfaces 61a, 63a, 61b, 62b, and 63b except for the incident surface 62a of the anticorrosion member 62 travel in directions crossing the light axis, respectively. As a result, the effect of multireflection can be suppressed to reduce the variation in the light amount of light detected in every reference measurement cycle.

As can be seen from the variations described above, as long as any one of adjacent surfaces selected from among the incident surfaces and emitting surfaces of all the translucent members constituting the reference cell is tilted with respect to the light axis of the light passing through the reference cell, the effect of multireflection occurring due to a reflection light generated at at least a surface positioned on the light detector side between the adjacent surfaces can be reduced.

Figure 5A:
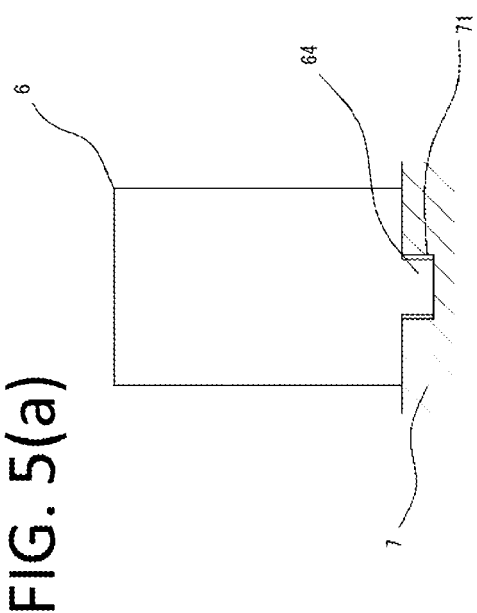
FIGS. 5(a) and 5(b) are schematic diagrams illustrating an example of a guide in each of still other variations of the present invention.
Figure 5B:
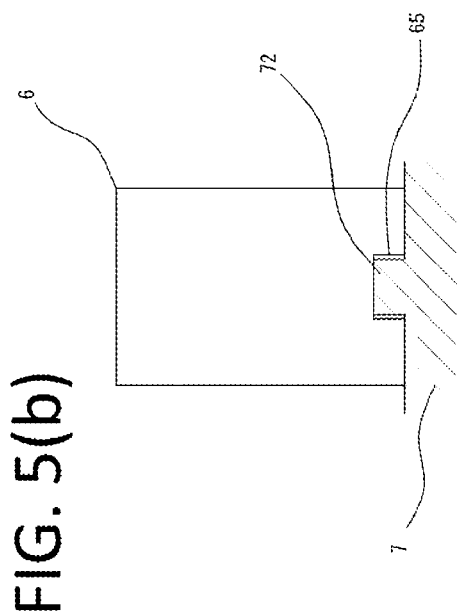

In addition, as the guide, for example, as illustrated in FIG. 5(a), a configuration adapted to slide a protrusion 64 provided on the reference cell 6 along a rail groove 71 provided in a main body 7 of the absorption spectrometer 100, or as illustrated in FIG. 5(b), a configuration adapted to slide a rail groove 65 provided in the reference cell 6 and the sample cell 5 along a protrusion 72 provided on the main body 7 of the absorption spectrometer 100 is conceivable. Alternatively, it may be configured to make the rotational transfer between the retracted position and the measurement position by a rotation mechanism.

In addition, it may be configured to move the light source side with the reference cell 6 and the sample cell 5 fixed, and even such a configuration makes it possible to produce the same effect.

LIST OF REFERENCE CHARACTERS

2: Light source
4: Light detector
5: Sample cell
6: Reference cell
61: Dimming member (translucent member)
62, 63: Anticorrosion member (translucent member)
61a, 62a, 63a: Incident surface
61b, 62b, 63b: Emitting surface
100: Absorption spectrometer

The invention claimed is:

1. An absorption spectrometer comprising:
   a light source;
   a light detector adapted to detect light emitted from the light source;
   a sample cell adapted to be selectively arrangeable either a sample measurement position positioned in a light path of the light passing between the light source and the light detector or a sample retracted position retracted from the sample measurement position; and
   a reference cell adapted to be selectively arrangeable either a reference measurement position positioned in the light path of the light passing between the light source and the light detector or a reference retracted position retracted from the reference measurement position, and contain at least one translucent member that transmits the light traveling along the light path from an incident surface to an emitting surface in a state of being arranged in the reference measurement position, wherein
   at least one surface selected from among the incident surface and the emitting surface of the translucent member constituting the reference cell is tilted with respect to a light axis of the light traveling along the light path.

2. The absorption spectrometer according to claim 1, wherein
   the reference cell is adapted to be slidable along a guide bridging between the reference measurement position and the reference retracted position.

3. The absorption spectrometer according to claim 1, wherein
   at least one pair of surfaces selected from among incident surfaces and emitting surfaces of all translucent members constituting the reference cell is parallel, and the paired surfaces are both tilted with respect to the light axis of the light traveling along the light path.

4. The absorption spectrometer according to claim 1, wherein
   incident surfaces and emitting surfaces of all translucent members constituting the reference cell are parallel.

5. The absorption spectrometer according to claim 1, wherein
   at least one pair of surfaces selected from among incident surfaces and emitting surfaces of translucent members constituting the reference cell is nonparallel, and any one or both of the paired surfaces are tilted with respect to the light axis of the light traveling along the light path.

6. The absorption spectrometer according to claim 1, wherein
   incident surfaces and emitting surfaces of all translucent members constituting the reference cell are nonparallel.

* * * * *